United States Patent
Azpiroz et al.

(10) Patent No.: US 9,901,926 B2
(45) Date of Patent: Feb. 27, 2018

(54) MICROFLUIDIC CHIP WITH DIELECTROPHORETIC ELECTRODES EXTENDING IN HYDROPHILIC FLOW PATH

(71) Applicants: INTERNATIONAL BUSINESS MACHINES CORPORATION, Armonk, NY (US); IBM RESEARCH GMBH, Rueschlikon (CH); SIX SEMICONDUTORES, Rio de Janeiro (BR)

(72) Inventors: Jaione Tirapu Azpiroz, Rio de Janeiro (BR); Emmanuel Delamarche, Rueschlikon (CH); Tobias Guenzler, Rio de Janerio (BR); Govind Kaigala, Rueschlikon (CH); Yuksel Temiz, Rueschlikon (CH); Tino Treiber, Rio de Janerio (BR)

(73) Assignee: International Business Machines Corporation, Armonk, NY (US)

( * ) Notice: Subject to any disclaimer, the term of this patent is extended or adjusted under 35 U.S.C. 154(b) by 118 days.

(21) Appl. No.: 14/901,695

(22) PCT Filed: Jun. 18, 2014

(86) PCT No.: PCT/IB2014/062345
§ 371 (c)(1),
(2) Date: Dec. 28, 2015

(87) PCT Pub. No.: WO2014/207618
PCT Pub. Date: Dec. 31, 2014

(65) Prior Publication Data
US 2016/0367988 A1    Dec. 22, 2016

(30) Foreign Application Priority Data
Jun. 28, 2013 (GB) .................................. 1311679.3

(51) Int. Cl.
*G01N 27/447* (2006.01)
*G01N 27/453* (2006.01)
(Continued)

(52) U.S. Cl.
CPC ... *B01L 3/502761* (2013.01); *B01L 3/502707* (2013.01); *B03C 5/005* (2013.01);
(Continued)

(58) Field of Classification Search
CPC ............................................. B03C 5/00–5/028
See application file for complete search history.

(56) References Cited

U.S. PATENT DOCUMENTS 6,416,642 B1 * 7/2002 Alajoki ............... B01J 19/0093
                                                            204/451
7,682,817 B2    3/2010 Cohen et al.
(Continued)

FOREIGN PATENT DOCUMENTS

EP         2 047 910 B1    1/2012
WO   WO 2007/021762 A2    2/2007
(Continued)

OTHER PUBLICATIONS

Morishima et al. "Novel Separation Method on a Chip Using Capillary Electrophoresis in Combination with Dielectrophoresis," Micro-Total Analysis Systems 2000, 269-272.*
(Continued)

*Primary Examiner* — Alexander S Noguerola
(74) *Attorney, Agent, or Firm* — Scully, Scott, Murphy & Presser, P.C.; Kurt Goudy, Esq.

(57) ABSTRACT

The present invention is notably directed to a microfluidic chip (1, 1a) comprising: a flow path (22) defined by a hydrophilic surface; a liquid input (24, 24a, 24b) on one side of the flow path; at least one electrical circuit (62), hereafter DEP circuit, comprising at least one pair of dielectrophoretic electrodes (E21, E22), hereafter DEP electrodes, wherein: each of the DEP electrodes extends transverse to the flow path; and the DEP circuit is configured to generate a dielectrophoretic force, hereafter DEP force, at the level of the DEP electrodes. The chip may further include one or
(Continued)

more electroosmotic circuits. The present invention is further directed to methods of operation of such a microfluidic chip.

19 Claims, 6 Drawing Sheets

(51) Int. Cl.
*B01L 3/00* (2006.01)
*B03C 5/00* (2006.01)
*B03C 5/02* (2006.01)

(52) U.S. Cl.
CPC ....... *B03C 5/026* (2013.01); *G01N 27/44713* (2013.01); *G01N 27/44717* (2013.01); *G01N 27/44743* (2013.01); *G01N 27/44791* (2013.01); *B01L 2200/0668* (2013.01); *B01L 2300/0877* (2013.01); *B01L 2300/0883* (2013.01); *B01L 2400/0406* (2013.01); *B01L 2400/0418* (2013.01); *B01L 2400/0424* (2013.01); *B03C 2201/26* (2013.01)

(56) References Cited

U.S. PATENT DOCUMENTS

| | | |
|---|---|---|
| 8,228,657 B2 | 7/2012 | Jones et al. |
| 2003/0083401 A1* | 5/2003 | Schneider .............. B82Y 30/00 523/313 |
| 2003/0138969 A1* | 7/2003 | Jakobsen .............. B01L 3/5027 436/180 |
| 2004/0011650 A1* | 1/2004 | Zenhausern ...... B01L 3/502746 204/547 |
| 2006/0091015 A1* | 5/2006 | Lau ................... B01L 3/502707 204/643 |
| 2012/0028342 A1 | 2/2012 | Ismagilov et al. |

FOREIGN PATENT DOCUMENTS

| | | |
|---|---|---|
| WO | WO 2007/046485 A1 | 4/2007 |
| WO | WO 2009/139124 A1 | 11/2009 |

OTHER PUBLICATIONS

EPO computer-generated English language translation of JP 2008-130083, downloaded Jun. 20, 2017.*

EPO computer-generated English language translation of JP 2005-305049, downloaded Jun. 20, 2017.*

Jiang et al., "Research of Dielectric Breakdown Microfluidic Sampling Chip", Hindawi Publishing Corporation, Journal of Nanomaterials, vol. 2013, Article ID 876829, 5 pages; Accepted Feb. 1, 2013.

Chen et al., "Electrokinetically driven flow control using bare electrodes", in Microfluidics and Nanofluidics, Jul. 2007, Springer-Verlag 2007.

* cited by examiner

FIG. 10 too long surface in the flow path, the misalignment between the exposed electrode surface and the surrounding surface being preferably less than 20 nm, and more preferably less than 10 nm.

In preferred embodiments, electrodes of one or more electrical circuits of the chip form a repeating pattern of pairs of contiguous electrodes, the electrodes of said pairs of contiguous electrodes being different, preferably having different dimensions and more preferably made, each, essentially of aluminum.

Preferably, the chip further comprises at least one additional electrical circuit, hereafter control circuit, having at least one pair of control electrodes extending in the flow path, and further configured to detect a change in an electrochemical or a physical property of a liquid flowing at the level of said pair of control electrodes, said control circuits preferably coupled to provide inputs to the EO circuit, and more preferably to the DEP circuit as well.

In embodiments, at least one pair of DEP electrodes of a DEP circuit of the chip is closer to the liquid input than at least one pair of EO electrodes of a EO circuit of the chip, and wherein, preferably, every pair of DEP electrodes is closer to the liquid input than any pair of EO electrodes.

Preferably, said EO circuit is a first EO circuit comprising at least a first pair of EO electrodes, and the chip further comprises an additional EO circuit comprising at least a second pair of EO electrodes that extend, each, transverse to the flow path, said first pair of EO electrodes and said second pair of EO electrodes being configured to generate opposite EO forces, and wherein, preferably, at least one pair of DEP electrodes is between said first pair of EO electrodes of said first EO circuit and said second pair of said second EO circuit.

In preferred embodiments, the chip comprises a passive capillary pump in fluid communication with the flow path, and an EO circuit of the chip comprises one or more pair of EO electrodes extending, each, in the capillary pump.

Preferably, the chip comprises a microfluidic microchannel, defining said hydrophilic flow path, and being in fluid communication with a liquid loading pad at one end and with a capillary pump at another end, wherein the chip further comprises a dry-film cover sealing the microfluidic microchannel and the capillary pump, an air vent being preferably provided in fluid communication with the capillary pump.

In embodiments, the chip comprises a microfluidic microchannel, defining said hydrophilic flow path, said microchannel further exhibiting lateral slanted walls, at least one, preferably each, of the electrodes of the DEP circuit and/or an EO circuit of the chip being a multiwall electrode, extending at least partly across the hydrophilic surface and one or each of said slanted walls, level with a surrounding surface.

According to another aspect, the invention is embodied as a method of operating a microfluidic chip according to any one of the above embodiments, wherein the method comprises:

injecting at the liquid input a liquid comprising a suspension of particles, such as functionalized microbeads;

letting the liquid wet and advance along the hydrophilic flow path and, preferably, get capillary pulled by a passive capillary pump of the chip, in fluid communication with the flow path;

energizing the DEP circuit for trapping particles at the DEP electrodes, preferably via a DEP signal generator coupled in the DEP circuit to provide a first AC signal to the DEP electrodes, by modulating an amplitude and/or a frequency of the first AC signal to modulate the DEP force as necessary to trap particles, wherein the DEP trapping is preferably accomplished while modulating an amplitude and/or a frequency of a second AC signal provided to EO electrodes of an EO circuit of the chip, via an EO signal generator coupled in the EO circuit, to modulate the EO force and obtain an EO force sufficient to alter a flow of liquid advancing in the hydrophilic flow path.

Devices and methods embodying the present invention will now be described, by way of non-limiting examples, and in reference to the accompanying drawings. Technical features depicted in the drawings are not to scale.

BRIEF DESCRIPTION OF SEVERAL VIEWS OF THE DRAWINGS

FIGS. 2A-D are 3D views of a simplified representation of a chip, according to embodiments.

DETAILED DESCRIPTION OF THE INVENTION

The following description is structured as follows. First, some difficulties that present inventors observed with conventional methods are discussed. General embodiments of the proposed solution, emphasizing prominent features of this invention, and high-level variants are then described (sect. 2). The next section addresses fabrication methods, specific embodiments and technical implementation details (sect. 3).

1. Difficulties Observed with Conventional Methods and Devices

CDF Microfluidic Devices

A number of microfluidic devices enabling capillary-driven flows (CDFs) have been developed. But such devices usually have one or more of the following drawbacks:

Capillary pressure is pre-defined by the wetting characteristics of the flow path;

Capillary pressure is encoded in the design;

It is not possible to vary the flow rates of samples to optimize assays using the same microfluidic chip.

The wetting characteristics of some materials used for making the chip will pose problems (too much or insufficient wettability), and;

Exposure of surfaces of the flow path to ambient conditions can alter the original wetting characteristics of these surfaces, e.g. contamination of the surfaces.

EO/DEP Devices

Present inventors have considered and studied known EO/DEP devices and concluded that such devices usually have the following drawbacks:

They require a very high voltage in some cases to be effective;

They are inefficient with initial filling of a chip when only a few electrodes are wetted ('priming');

They are prone to adverse electrochemical reactions, especially when a DC potential is used.

They have therefore explored new directions, both in terms of fabrication and designs, notably allowing for more flexibility and operating with more diverse types of samples and flow conditions. Embodiments of the invention discussed herein solve one or more of the above issues.

2. General Embodiments and High-Level Variants

In reference to FIGS. 1-9, 11, an aspect of the invention is first described, which concerns a microfluidic chip 1, 1a. This chip essentially comprises:

A flow path 22 defined by a hydrophilic surface;

A liquid input 24, 24a, 24b on one side of the flow path; and

At least one electrical circuit 62, hereafter refereed to as "DEP circuit", which circuit comprises one or (likely) more pairs of dielectrophoretic electrodes E21, E22, hereafter referred to as DEP electrodes.

Remarkably, each of the DEP electrodes extends transverse to the flow path, which is defined by a hydrophilic surface, contrary to conventional DEP devices. The DEP circuit is generally configured to generate a dielectrophoretic force (or DEP force), at the level of the DEP electrodes E21, E22.

The flow path 22 is preferably capillary-driven, thanks to a capillary pump (which can be regarded as a flow path too) provided in fluid communication with the flow path, resulting in a capillary driven flow (hereafter CDF). Since the flow path is hydrophilic, a liquid fed into the flow path shall anyway wet the hydrophilic surface and advance in the flow path. The flow path is preferably provided in a closable microchannel 20, e.g., grooved in or structured on top of a surface of the chip, as discussed later. Note that the flow path is "hydrophilic" inasmuch as it is defined by (at least) one hydrophilic surface. The flow path may nevertheless be defined by several surfaces, but not all these surfaces need to be hydrophilic. Hydrophilicity of the flow path can be achieved by a combination of hydrophilic and hydrophobic surfaces or by having surfaces with various hydrophilic characteristics.

The liquid input may for instance be a liquid loading pad 24, configured for loading liquid sample into the flow path, but could also be a microchannel, e.g., itself in communication with a liquid loading pad or another flow path, or any kind of liquid inlet (preferably a compact inlet).

Importantly, electrodes E21, E22 are provided in the flow path and extend, each, transverse to the main direction of the flow path, in contrast with known devices. The idea is to use DEP concurrently with CDF, to be able to trap particles p, e.g., functionalized microbeads suspended in liquid e.g., water while filling the flow path. The DEP force must thus be sufficient to trap the particles. Meanwhile, CDF helps with initial filling of the chip, even if no or few electrodes are wetted.

Note that electrode may not fully extend transversely through the channel 20. First this is not needed in all application (though preferred in some cases). Second, it may be desirable to leave a bit of space in the channel without electrode for detection purposes, e.g., optical fluorescence detection.

Figure 3:
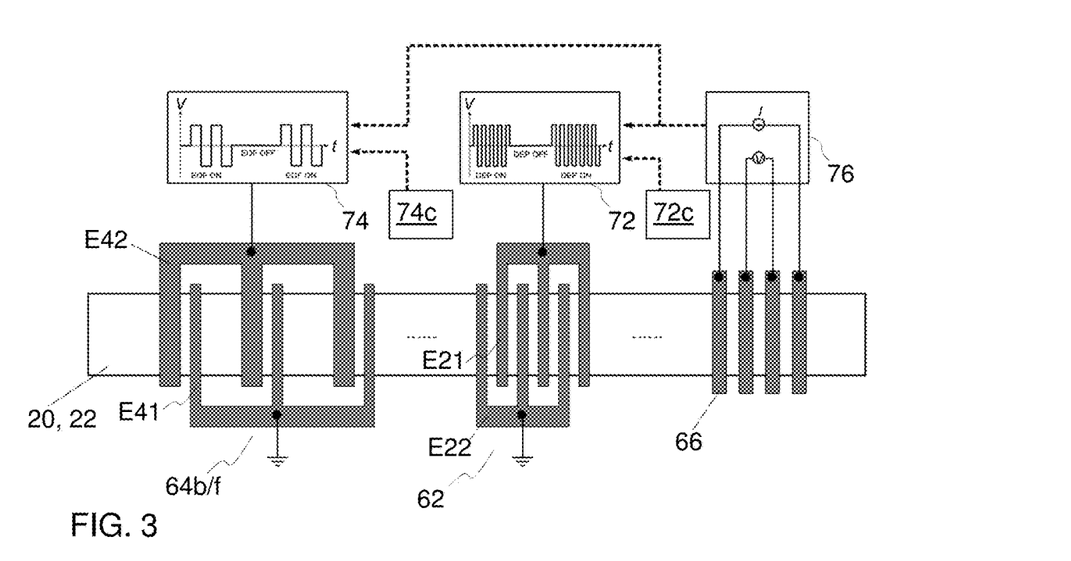
FIGS. 3-4 schematically illustrate selected components, including DEP and EO circuits, of chips, as involved in embodiments.

Referring now to FIG. 3, the DEP circuit preferably comprises a DEP signal generator 72, coupled in the DEP circuit to provide an AC signal to the DEP electrodes E21, E22. The DEP signal generator 72 is configured to enable modulation 72c of an amplitude and/or a frequency of the AC signal, such that the DEP force can be modulated.

A DC signal can in principle be used but the voltage required is so high that it makes it difficult for microfluidic applications, as present inventors concluded from various tests. The literature suggests that DC can be used. However, above 3V DC, bubble generation electrolysis or electrochemistry effects can be expected, depending on the electrode material, liquid, and the gap between the electrodes used. On the other hand, in AC DEP, the potential can easily be increased up to 20 Volts peak-to-peak (or Vpp). Therefore, an AC signal is much preferred. The signal generator makes it possible to adapt the DEP force necessary for trapping various types of particles, e.g., microbeads about the electrodes E21, E22. A polarizable particle exposed to a non-uniform AC electric field experiences dielectrophoresis: the particle becomes polarized and is subjected to an electric force. A microbead in a liquid can be moved in a microfluidic channel using DEP. The microbead migrates in the electric field and rests in a field gradient minima or maxima. Therefore, beads p carrying receptors for analytes can be added to a sample and trapped in a microchannel (see e.g., FIG. 2C), which in turn allows for measuring/detecting analytes on the surface of the beads.

Optimal ranges for the amplitude/frequency primarily depend on the liquid/particle properties and electrode geometry. Inventors observed a DEP effect when using typically 5 Vpp to 20 Vpp voltage amplitudes and 100 kHz to 10 MHz frequencies. More specifically, 10-15 Vpp at 0.5-2 MHz was usually found to be most satisfactory, giving best results notably for applications such as evoked in the next section.

Now, for some repetitive or -predefined applications, a fixed amplitude/frequency signal could be relied upon, without it being necessary to modulate the signal, such that no amplitude/frequency modulation would be needed in that case. Instead, a circuit generating a signal having predefined, non-modifiable characteristics would suffice.

Referring now to FIGS. 1-4 and 11, the microfluidic chip 1, 1a preferably comprises one, more preferably two (or more) electroosmotic (EO) circuits 64b, 64f. EO circuits comprise one or (more likely) more pairs of EO electrodes E41, E42, which, again, extend transverse to the flow path 22. The EO electrodes are distinct from the DEP electrodes, i.e., they are arranged at distinct locations in the flow path 22. Such EO circuits are configured to generate an EO force, by way of EO electrodes and signals applied thereto.

An EO circuit preferably comprises an EO signal generator 74, coupled to provide an AC signal to the EO electrode E41, E42. The EO signal generator 74 is generally configured to enable modulation 74c of an amplitude and/or a frequency of the AC signal provided to EO electrodes, such that the EO force can be modulated too.

By "signal generator" (also called function generator, waveform generator, or frequency generator), it is meant any device capable of generating a signal and configured to enable modulation of the amplitude and/or the frequency of the AC signal. Most common waveforms, such as a sine wave, sawtooth, step (pulse), square, or triangular waveform can be used.

Just like for DEP electrodes, EO electrodes are preferably interdigitated, as illustrated in the appended drawings: opposite combs connect opposite electrodes such as to form EO electrode pairs. Interdigitated geometry of opposing electrodes has advantages in terms of compactness, and fabrication process. Since AC current is preferably used, one EO electrode of one pair, connected via one comb, becomes positive, while the other electrode of the same pair (yet connected to an opposite comb) becomes negative, and this periodically switches.

The amplitude (which impacts the voltage of the AC signal applied to electrodes) and/or the frequency of the AC signal can be changed to modulate the EO force. Other EOF generation techniques, such as travelling-wave EOF, may require phase modulation as well; however, this technique requires higher number of electrical contacts and metal layers compared to AC EOF. Additional phase modulation is therefore not preferred, though not excluded. A sufficient EO force (or EOF) should be achieved, such as to be able to alter a flow of liquid e.g., comprising water or anyhow able to wet a hydrophilic surface in the hydrophilic flow path, e.g., while being capillary driven therein. The idea here is to use the EOF to modulate the CDF (which typically remains the main liquid driving force, still helping with initial filling of the chip), concurrently with the DEP force, such that a better tuning of the DEP trapping can be obtained. Thanks to the DEP circuit, particles typically—but not necessarily—align along inner peripheries of pairs of DEP electrodes. Thanks to the EO circuit, the EO force will result in an EOF flow, ions will show a propensity to go in one or the other direction in the flow path.

An additional advantage of such a device is that, since EO is used in addition to CDF, EO may or may not be activated. Thus, if adverse electrochemistry is expected, EO electrodes may simply not be energized. In this respect, control electrodes may be provided too, as to be discussed later.

Using AC modulation, one can operate DEP and EOF simultaneously; both sets of electrodes can be controlled at the same time. Frequencies used for the respective circuits typically differ by orders of magnitude e.g., at 1 kHz and 1 Mhz, respectively. Thus, the DEP and EO circuits are designed to provide signals that markedly differ: a circuit configured for DEP and in particular a DEP signal generator may not necessarily be adapted for EOF, and conversely. Typical amplitude/frequency ranges for each circuit are the following:

DEP: 100 kHz to 10 MHz, with 5 Vpp to 20 Vpp pp: peak to peak, typically 1 MHz is applied. Optimal voltage depends on the flow rate, particle size, liquid properties, etc. Generally, 10 Vpp is sufficient for most cases, e.g., for 10 μm beads in 1×TAE buffer, with flow rates lower than 100 μm/sec; and EOF: 100 Hz to 10 kHz, 1 Vpp to 10 Vpp. Typically, a frequency of 1 kHz is applied, while the voltage is lower than or equal to 10 Vpp, otherwise bubble generation occurs at such lower frequencies.

Again, A DC signal could in principle be used for the EO circuit too but this is undesired in the present context, as present inventors concluded, for similar reasons as for DEP.

EO and DEP electrodes are preferably different (dimension, shape: asymmetric vs. symmetric, material, . . . ) and optimized to best fulfill their respective purposes. In the present case, for instance, using asymmetric EO electrodes and an AC field, EOF can be made unidirectional, whereas symmetric electrode pairs are best suited for DEP (though asymmetric electrodes may work for DEP too even if suboptimal), as illustrated in FIG. 3.

Figure 1:
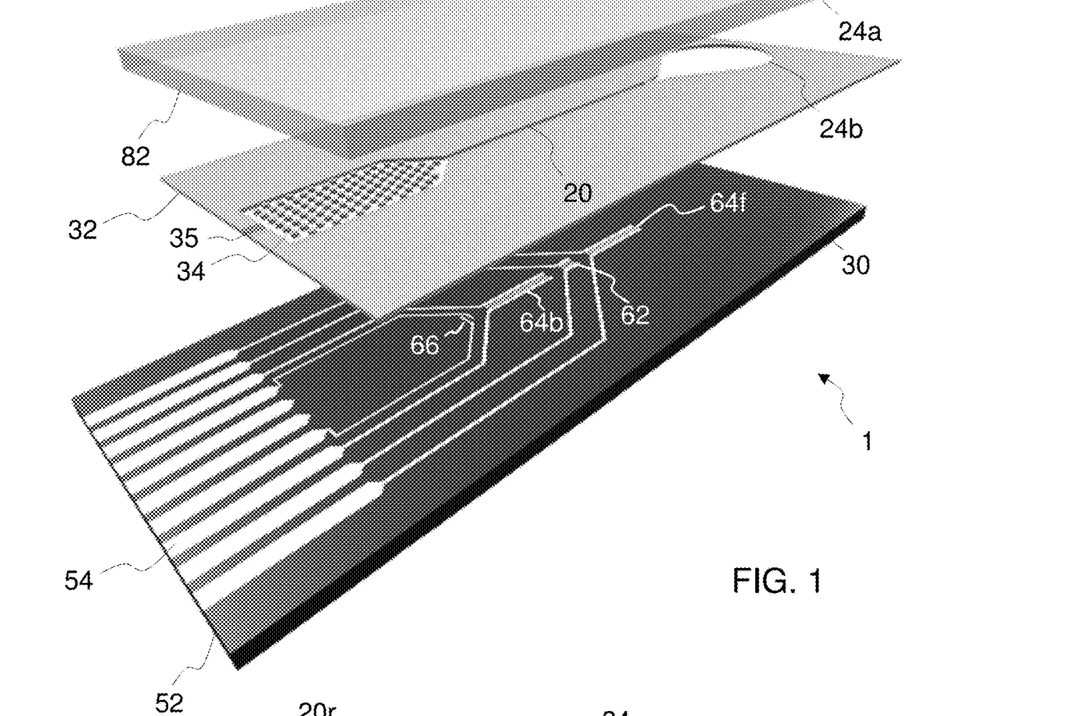
FIG. 1 is a 3D, exploded view of a microfluidic chip (simplified representation), showing relationship between various parts of this device, as in embodiments.
Figure 11:
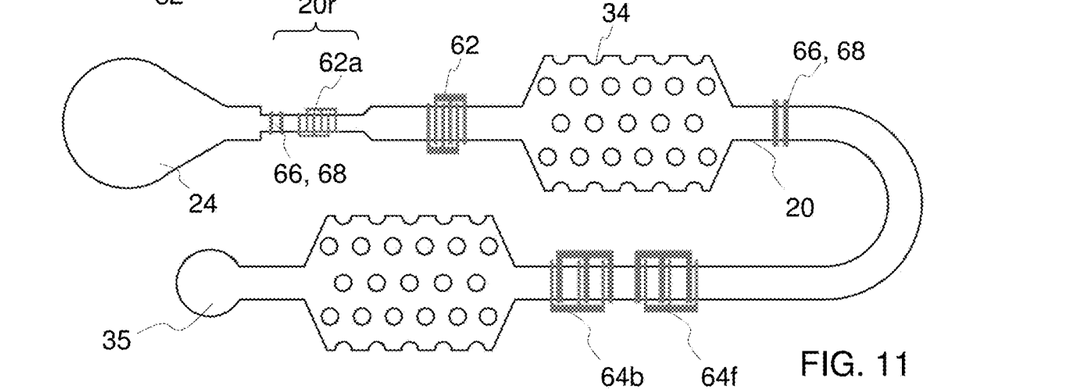
FIG. 11 schematically illustrates selected components of a chip wherein a microchannel has a reduced section at the level of DEP electrodes of a first DEP circuit, compared to the average microchannel section, as in embodiments.

Two EO circuits 64f, 64b are preferably provided, to be able to modulate the CDF in both directions, as illustrated in FIGS. 1, 2 and 11. We call forward EOF the EOF in the direction of the capillary pump 34 enabled by circuit 64f. Backward EOF circuit 64b directs toward the liquid input, e.g., the loading pad 24. EO electrodes of circuits 64f and 64b are accordingly configured to generate opposite EO forces. In addition, DEP electrodes can be located between EO electrodes of the circuit 64f and EO electrodes of circuit 64b, to achieve better flow control at the level of the DEP electrodes, as illustrated in FIGS. 1 and 2.

The DEP and EO electrical circuits are at least partly independent. However, the ground electrode may be common for both circuits. Not only this saves space on the chip but also it reduces the number of electrical contact pads 54, if needed. In this respect, it should be borne in mind that in the present context contact pads may occupy as much as 43% of the chip area.

More generally, optimization is desired inasmuch as it directly reduces manufacturing costs. Also, note that the chip may comprise several flow paths in parallel, similarly configured and with similar arrangements of electrodes (of any type: DEP, EO or control electrodes, as discussed later).

For completeness, the connection of electrodes to contact pads 54 may have some importance as it can substantially impacts the cost of chips. In this regard, the microfluidic chip may advantageously comprise electrical contacts mating with a socket. The contacts have preferably 500 μm width and 300 μm spacing, i.e. 800 μm pitch. The socket should preferably allow mechanical alignment of less than 200 μm to avoid short-circuits and wrong connections. As an example, HSEC8 type of edge connector from SAMTEC has 800 μm-pitch contacts and allows precise chip to socket alignment. For this socket, 4.5 mm long contact area is used for reliable electrical connection. Chips can be designed to have final width of 100 μm (50 μm from each side less than the socket opening to allow easy placement without giving damage to the socket or the chip). Variations in the chip dimensions during chip dicing are expected to be within 50 μm. The contacts are placed on one side of the chip, preferably away from the loading pad (opposite side for instance). The number of contacts can be increased by repetition (constant pitch) as long as the chip dimension allows. The number of contacts can be decreased by sharing the ground electrode of DEP and EO electrode sets. If the number of required contacts is less than the maximum number of contacts that the side of the chip can accommodate, then the unused contact areas can be used for microfluidic structures. Moreover, the same socket allows electrical connection to the backside of the chip in case a conductor or semiconductor, e.g. silicon, substrate is used and substrate biasing is required.

Referring now more particularly to FIGS. 6-9: the hydrophilic surface is much preferably defined in a microfluidic microchannel 20, and more precisely by one or more inner walls 22a, 22b, 22c of channel 20. Thanks to novel fabrication methods discussed in the next section, this surface can be made of $SiO_2$, by way of thermal oxidation (from a Si wafer), which allows for high quality $SiO_2$ layers to be obtained. Still, $SiO_x$ layers may be obtained that convenes too, using low temperature deposition techniques, like sputtering, evaporation. However, $SiO_x$ surfaces shall likely have higher defect density and pinholes, which may impair electrical insulation properties as sought in present applications. In variants, low-pressure chemical vapor deposition (LPCVD) of $Si_3N_4$ silicon nitride or atomic layer deposition (ALD) of dielectric layers, e.g., $Al_2O_3$, etc., can be contemplated too. ALD allows for high quality dielectric layers to be obtained. However, ALD is an expensive technique, with which thick layers, such as 50 nm or higher, may not be feasible. More shall be said on fabrication methods in section 3.1.

Figure 7:
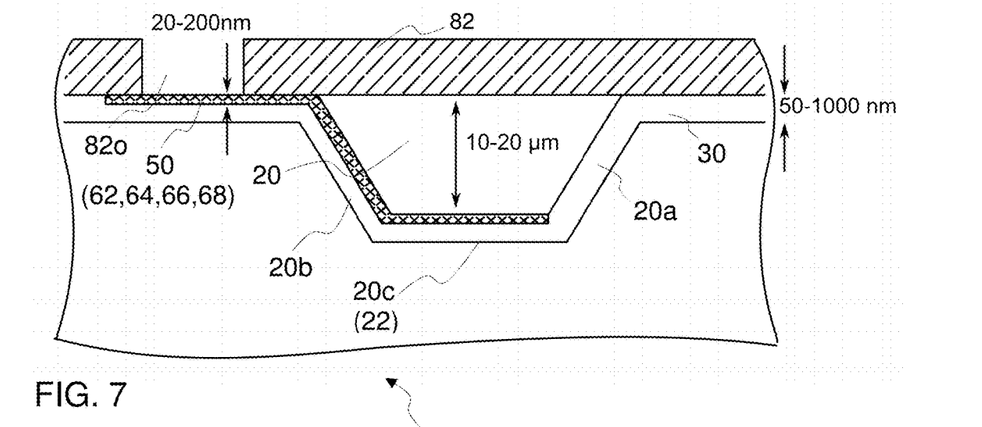
FIG. 7 is a 2D cross-sectional view (partial) of a simplified representation of a microfluidic chip, comprising a cover sealing microstructures of the chip, according to embodiments.
Figure 8:
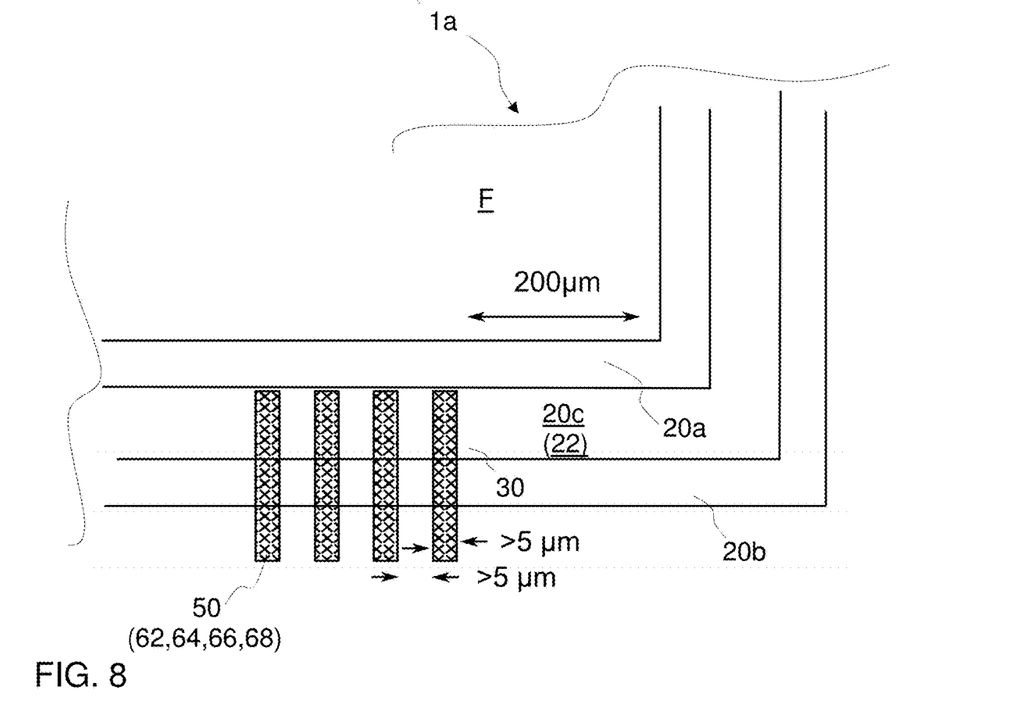
FIG. 8 is a 2D view (partial), from above, of the microfluidic chip of FIG. 7.

Some of these fabrication methods allow for obtaining flush electrode surfaces. Namely, the surface of an electrode 50 (which could be any DEP, EO or control electrode) extending transverse to the flow path 22, that is exposed to fluid (in operation), can be fabricated such as to be level with a surrounding surface in the flow path. In other words, electrodes preferably are arranged in the channel 22 such as to be integrated within a superficial thickness of surfaces of the channel that define the flow path 22, the exposed surfaces of electrodes being flush with the surrounding surface 30, see FIGS. 6-9. This means that the misalignment between an exposed electrode surface and the surrounding surface is negligible with respect to the depth of the microchannel (preferably 2, and ideally 3 orders of magnitude below or less). For instance, methods described in sect. 3.1 allow for achieving misalignments that are less than 20 nm, and even less than 10 nm, whereas the channel depth typically is between 10 and 20 μm. This minimizes surface topography and thus favors laminar flows, which may be advantageous to prevent sticking of cells, beads or other particles along the flow path. Minimized surface topography is also advantageous to avoid pinning sites during the initial filling of a flow path by a liquid. This also reduces edge-defects on the electrodes and thus prevents spurious electric fields at the edges. It further favors efficient sealing by a cover 82 put on top, as illustrated in FIG. 7.

Figure 9:
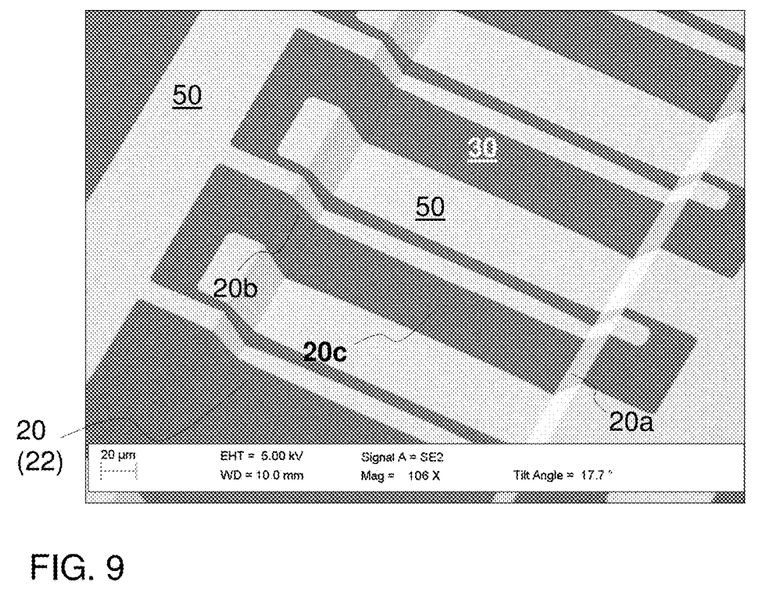
FIG. 9 is a scanning electron microscope image of a microchannel of a microfluidic chip, wherein electrodes extend through the channel, level with walls thereof, as in embodiments.

The SEM image shown in FIG. 9 illustrates the quality of interfaces obtained. In this image:
EHT stands for Electron High Tension in kilo-Volt, kV;
WD denotes the working distance between the sample surface and the low portion of the lens;
Mag is for magnification;
Tilt Angle denotes the angle of the normal of the sample stage with respect to the axis of the electron gun; and
Signal A=SE2 indicates that a detector of secondary electrons is used.

Referring now to FIGS. 1, 2, 7 and 11: as evoked earlier, the microchannel 20 is preferably in fluid communication with a passive capillary pump 34. Passive capillary pumps are known per se. In the present context, the passive capillary pump is dimensioned and structured to be able to capillary-drive a flow of liquid (e.g., comprising water or anyhow able to wet the hydrophilic flow path 22), i.e., beyond the capillary force exerted by the flow path itself. The liquid input 24 is preferably embodied as a liquid loading pad 24, opposite to the capillary pump 34 with respect to the microchannel 20.

The use of passive capillary pumps allows for creating a more compact, autonomous and efficient system. Preferably, no active pumping (forced liquid injection, extraction by liquid pumping or centrifugation) is present beyond the EO means, to achieve a more compact surface. In addition, the microfluidic chip does preferably not comprise any liquid connection to external devices e.g., via tubing ports, but rather is provided with just a liquid loading pad 24. For similar compactness reason, the chip does preferably not comprise any tank thereon.

Note that one or more pairs of EO electrodes could be placed in a capillary pump (not shown). Since a capillary pumps is larger than a microchannel, long electrodes running across the pumps may be more efficient for EOF generation, though more challenging to pattern. In variants, all EO electrodes could be provided in capillary pump segments, inserted in-channel or at an end of a channel 20 (not shown). In this regard, the chip may further comprise several capillary pumps arranged along the flow path, as shown in FIG. 11. In that case, at least one capillary pump is preferably located between at least one pair of EO electrodes and at least one pair of DEP electrodes.

An intermediate capillary pump facilitates the addition of two different liquids: since many liquids are detrimental to EO flow due to adverse corrosion of EO electrodes or due to the generation of gas bubbles, a user may want to screen EO electrodes with an EO-compatible liquid. EO-compatible liquids are for example liquids used in standard capillary electrophoresis. In this case, the EO-compatible liquid is added first followed by the addition of a liquid of interest (i.e. containing analytes, reagents and/or beads). However, microchannels in microfluidics typically have volumes of a few nanoliters up to a few hundred of nanoliters. Therefore, in absence of intermediate capillary pump, one may need to add not more than nanoliter volumes of an EO-compatible liquid (the first liquid) before adding a sample to the loading pad. Pipetting nanoliter volumes of liquids into microfluidics without the help of expensive peripherals is often impractical and not precise. An intermediate capillary pump is therefore advantageous because it adds a volume to the flow path that is significant enough (e.g., from 200 nanoliters up to a few microliters) to make the addition of liquid to the loading pad of the microfluidic chip easy and practical.

The chip may further comprise a cover 82 sealing microstructures of the chip, e.g., the microchannel 20 and the capillary pump 34, as seen in FIGS. 1 and 7. The cover may be hydrophilic, or not (not all surfaces defining the flow path need be hydrophilic, as said earlier). It anyhow contributes to define the flow path 22, even if the latter is mainly defined by walls of the microchannel 20. The cover can for instance be hydrophobic as long as the effective wetting is still favorable. However, the cover should not contaminate the channels, at least in some applications. Beyond the microfluidic microchannel and the capillary pump, the cover may more generally seal all microstructures about the microchannel. The cover may be machined to provide openings 82o (FIG. 7), be it for electrical contact (not shown), liquid inlet 24a (FIG. 1), air vent, etc.

Referring now more specifically to FIG. 11: a transverse section 20r of the microchannel may substantially differ at the level of DEP electrodes of a DEP circuit 62a of the chip 1a, compared to the average transverse section of the microchannel 20. The section variation allows for discriminating among large and small beads. A narrower section results in faster flows, which allows for trapping the largest particles. A wider section leads to slower flows, allowing for trapping both large and small particles. Thus, one can trap various bead populations in parallel.

In more detail, varying the width of the microchannel in the DEP electrode area locally changes the velocity of the liquid and therefore the hydrostatic pressure exerted on the particles (e.g., beads). Since the diameter of the beads affects directly the DEP force and liquid pressure on the beads, it is then possible to separate beads having different diameters. In a narrower channel, large beads will be trapped and small beads flushed. This opens the way to multiplexing and/or detecting a positive control and a signal control on at least two types of beads. Similarly, several channel section variations can be contemplated to discriminate several types of particles.

For completeness: the DEP force increases with the 3rd power of the bead radius. If one wants to trap beads that are 5, 4, 3 and 2 μm in radius, the DEP force will be respectively 125×, 64×, 27× and 8× compared to a 1 μm reference diameter. Therefore, one also needs to increase the channel width for trapping smaller beads so that the pressure of the liquid pushing the bead can scale down and not compromise the DEP force. A logical implementation is thus to provide a narrower region (for trapping large beads) upstream a larger region (for trapping smaller beads and remaining large beads, if any). Varying the transverse section $20r$ of the microchannel by a factor 2 shall already work in many cases. A factor of 3 is preferred inasmuch as it still allows for reasonably wide channels. More generally, this transverse section is typically between 1.5 and 4 times, more preferably between 2 and 3 times larger or smaller than the average section of the microchannel.

Several DEP circuits may accordingly be provided e.g., one per channel section variation, as illustrated in FIG. 11. In FIG. 11, a reduced section $20r$ is provided close to the liquid inlet 24 to trap largest particles via circuit/electrodes 62a, followed by an increased section for trapping smaller particles. For example, a 50 μm width may be used for reduced sections, while up to 500 μm can be contemplated for the wider sections. On average, a microchannel shall typically have a width between 100-200 μm. In this regard, since the depth of the channel typically is constant, the same factor applies to the widths as for the sectional areas of the channels. The average width or section of the microchannel that is taken for comparison pertains to channel segments excluding capillary pump segments (typically much wider than the average channel width).

Referring now to FIGS. 3-5, 9: electrodes (of any circuit) preferably form a repeating pattern of pairs of contiguous electrodes (each electrode of a pair connected to a respective comb), that extend transverse to the flow path 22. EO electrodes' pairs comprise electrodes that differ, e.g., having different dimensions, see FIG. 5. Electrodes are preferably made, each, essentially of aluminum. If the hydrophilic surface is a $SiO_2$ surface, then electrodes made of Al (50 nm, sputtered, with 5 nm Ti adhesion layer) are preferred, where Ti is used to enhance adhesion to $SiO_2$. Ti and Al can be deposited through two successive evaporation steps (without breaking vacuum between the two evaporation steps). Ti is nonetheless optional in that case as Al already exhibits good adhesion to $SiO_2$. However, a thin Ti layer would be needed for metallic electrodes made of metals like Au, Pt, Pd, etc. Excellent results have been obtained with other metals and with Pd in particular. Now, if there are no adverse electrochemical reactions expected at the metallic electrodes (due to the combination of liquid in the flow path and characteristics of the electrical signal applied to the electrodes) then Al is preferred because it is stable under ambient conditions, due to the formation of a self-limiting oxide layer on its surface. If adverse electrochemical reactions are expected, then palladium is preferred due to its excellent chemical stability and ability to hold hydrogen. Gold and platinum may also be used, instead of palladium.

Figures 5, 5A, 5B, 5C, 5D:
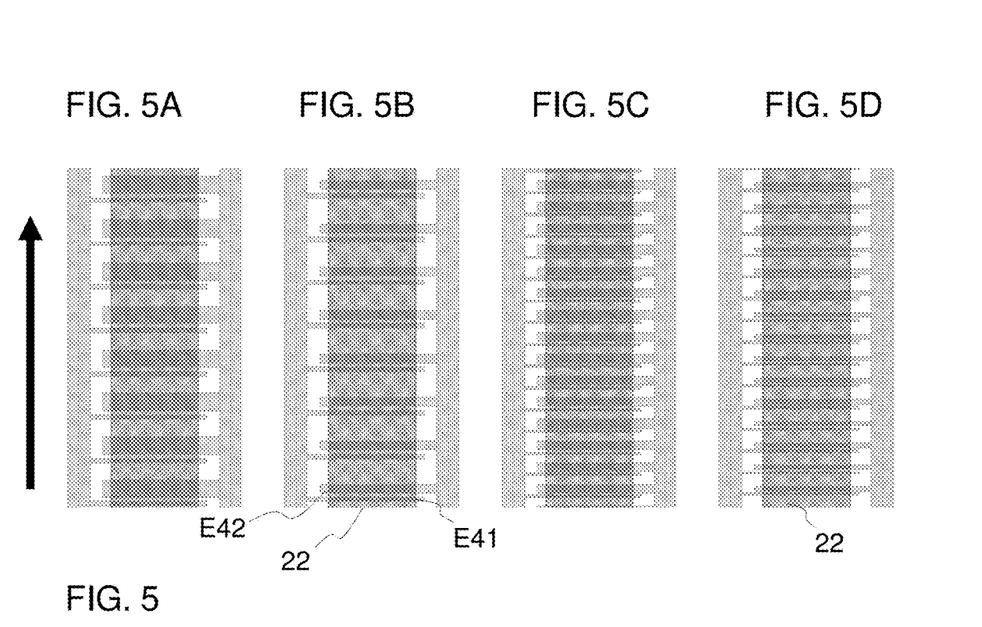
FIGS. 5A-D schematically illustrate various electrode pair patterns utilizable in embodiments.
Figure 6:
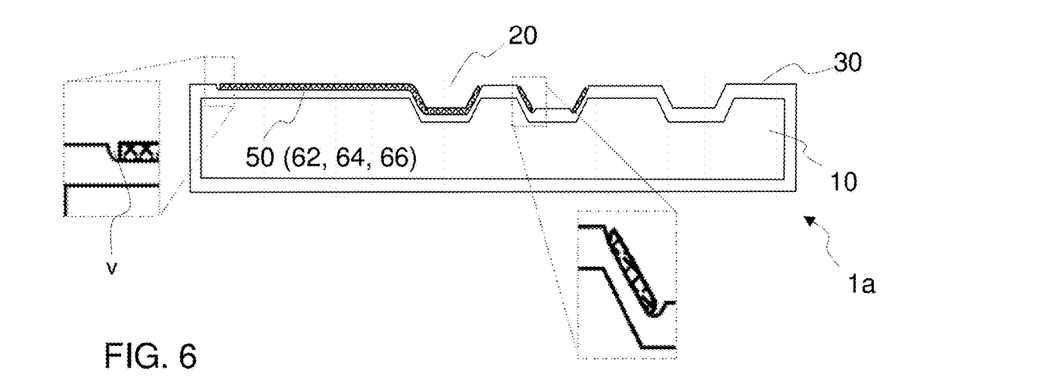
FIG. 6 is a 2D cross-sectional view (partial) of a simplified representation of a microfluidic chip, according to embodiments.

In FIG. 5: geometries A, B and C provide higher flow rates, while D results in (much) smaller EOF flows. Configuration of FIG. 5D is useful for finely tuned flow control, it being reminded that several EO circuits can be provided in series along a same microchannel. The electrode geometries are captured in Table I below:

TABLE I

| | electrode geometry of FIG. 5A-D | | | |
|---|---|---|---|---|
| Configuration | FIG. 5A | FIG. 5B | FIG. 5C | FIG. 5D |
| L: Width of large electrode (μm) | 40 | 20 | 20 | 10 |
| G: Gap between two paired electrodes (μm) | 10 | 10 | 5 | 5 |
| S: Width of small electrode (μm) | 10 | 10 | 5 | 5 |
| P: Pitch (μm) | 100 | 100 | 50 | 50 |

From values in Table I, one can infer preferred geometrical constraints. Namely: $L \in [10, 40]$; $G \in [5, 10]$, $S \in [5, 10]$, preferably $S = G$ and $L = n S$, with $n \in [2, 4]$, and $P \in [50, 100]$, preferably $P = 10 \times G$ (all in μm). Additional specifications for the configurations of FIGS. 5A-D follow:

Electrodes: Al (50 nm, sputtered, with 5 nm Ti adhesion layer);
Typical actuation: 10 Vpp amplitude, 1 kHz;
Substrate: 200 nm of thermal $SiO_x$ on a standard Si wafer, walls in SU-8, cover: PDMS elastomer; and
Microchannel: width 200 μm, height 18 μm, length 4 mm or more.

The above set of specifications was found most convenient for all tested applications.

Figure 4:
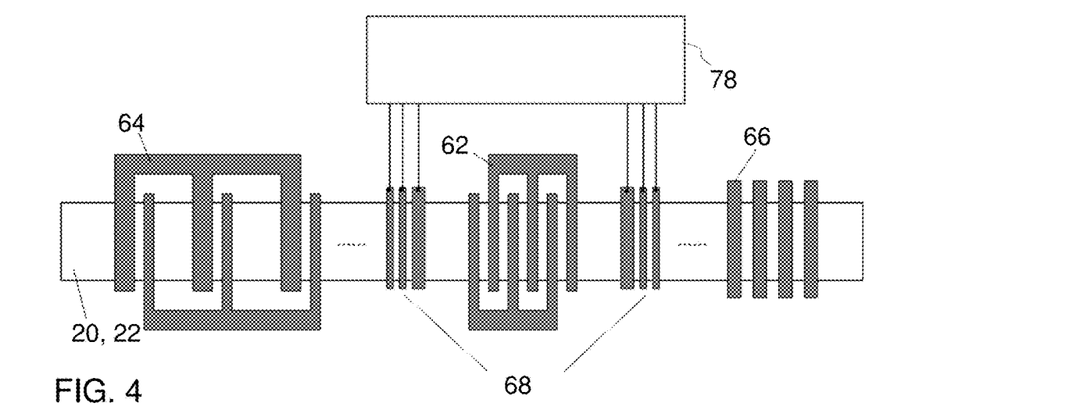

In reference to FIGS. 3, 4 and 11, the microfluidic chip may further comprise one or more control circuits 66, 76; 68, 78. A control circuit will comprise at least one pair of control electrodes 66, 68 extending transverse to the flow path, and be generally configured to detect a change in an electrochemical or a physical property of a liquid flowing at the level of the control electrodes. As illustrated in FIG. 3, a control circuit 66, 76 may be coupled to provide inputs to the EO circuit 64, 74, 74c, and to the DEP circuit 62, 72, 72c as well. The control circuit nevertheless remains at least partly independent from the DEP circuit and from the EO circuit, as illustrated in FIG. 3 or 4: the control electrodes are distinct from DEP and EO electrodes and can be distributed, at various locations, along the flow path.

The circuit 66, 76 represented in FIG. 3 may for instance be a physical control circuit, terminated by control electrodes 66. The circuit 66 may generally be configured to check the filling state of the microchannel (empty, or filled with liquid A, or liquid B). This can be done by measuring a change in conductivity or impedance, heat conduction, etc., and using a low potential (0.5 V or less to prevent electrochemistry). The physical control circuit 66, 76 may optionally be coupled to the DEP and EOF circuits 62, 64 to provide feedback and accordingly modify some properties of the AC signals, to take account of the filling state of the microchannel and automatically react. For instance, a counter EOF can be generated if it is detected that the liquid moves too fast for optimal trapping at the DEP.

An electrochemical control circuit 68, 78 (terminated by control electrodes 68) may be provided too (in addition to or instead of a physical control circuit), as seen in FIG. 4. This electrochemical circuit is configured to detect a change in a chemical composition of a liquid flowing at the level of the control electrodes 68. Preferably, at least some of the electrochemical control electrodes 68 are closer to the liquid input 24 than EO electrodes, and preferably closer to the liquid input than DEP electrodes too. The electrodes 68 may be closer to the liquid input than any of the EO electrodes and more preferably between at least one pair of DEP electrodes and one pair of EO electrodes. The control circuit 68, 78 too can be coupled to the DEP and/or EOF circuits 62, 64 to provide feedback and in turn modify properties of the AC signals provided to DEP and EO electrodes 62, 64.

The control electrodes and their respective circuits may be used to check for the arrival of a liquid and in particular if this liquid could compromise the EO/DEP electrodes. A minimal distance between a pair of control electrodes and a pair of EO/DEP electrodes could be imposed, to prevent ions of a liquid from reaching any one of the EO/DEP electrodes by passive diffusion.

In the embodiment of FIG. 11, DEP electrodes of circuits 62, 62a are closer to the liquid input 24 than EO electrodes of circuits 64b, 64f. Such a configuration is preferred when one wants to be able to trap particles as soon as possible.

Note that it is possible to have all electrodes drawn on the same mask layout and patterned at the same time through the same fabrication steps.

Figure 2A:
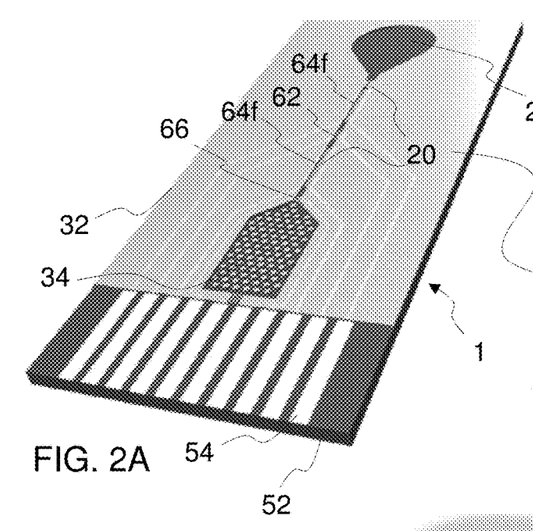
FIG. 2A is a view of an entire chip (not covered), while FIGS. 2B-D magnifies selected areas of FIG. 2A.
Figure 2B:
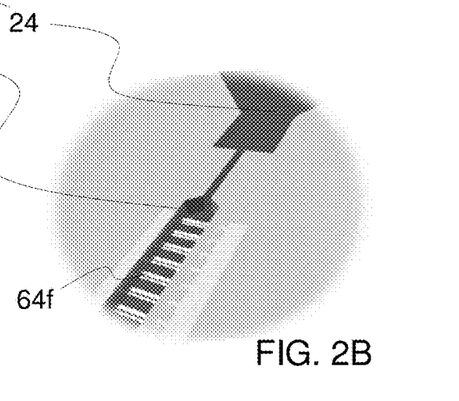
Figure 2C:
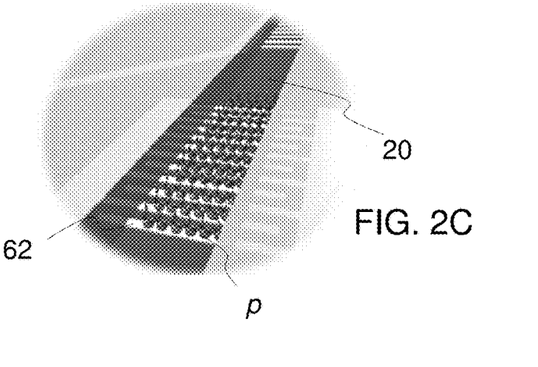
Figure 2D:
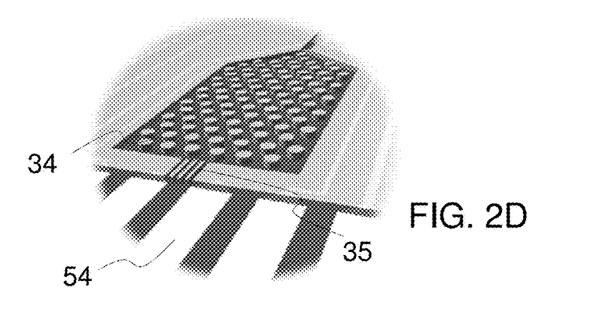

Several combinations of the features described above may be contemplated. Such features may furthermore be combined with other features illustrated in the appended drawings. For example, referring to FIGS. 1, 7, the microfluidic chip 1 may comprise a microfluidic microchannel 20, defining the hydrophilic flow path 22, in fluid communication with a liquid loading pad 24 at one end and with a capillary pump 34 at another end. The chip 1 may further comprise a dry-film cover 82, e.g., a dry-film cover sealing microfluidic structures, e.g., the microchannel 20 and the capillary pump 34. An air vent 35 is preferably provided, in fluid communication with the capillary pump. It prevents from too much air compression in the capillary pump while capillary pulling liquid in the microchannel. The air vent may for instance have a counterpart in the cover, for vertical evacuation (not shown). However, lateral evacuation 35 on the edge of the chip might be easier to fabricate since it does not require any patterning on the dry-film cover (as seen in FIG. 1 or 2D). Indeed, the air vent is made much smaller than the loading pad to minimize evaporation, therefore, it is not so easy to pattern on the cover film and align to the substrate.

At present, possible configurations of the electrodes in the channel 20 are described. Referring to FIGS. 6-9: a microfluidic microchannel 20 (defining the flow path 22) may exhibit lateral slanted walls 22a, 22b. At least one (but preferably each) electrode of the DEP circuit and/or an EO circuit may be configured as a multiwall electrode, i.e., the electrode extends at least partly across the hydrophilic surface (the bottom wall 20c in FIGS. 6-9) and one (or each) of the slanted walls 20a-b, flush with surrounding surface 30. That is, the exposed surface of this electrode is level with a surrounding surface 30, as explained earlier. For the DEP and EO electrodes, a minimum periphery covered by an electrode is preferably the following: an electrode shall at least extend through: (i) one slanted lateral wall (20a or 20b) plus (ii) at least partially transverse across the bottom wall 20c. When electrodes cover more than half the width of the bottom wall, then opposite electrodes become interdigitated. The resulting, effective EO or DEP force experienced by particles p will in that case be mostly parallel to the flow path, as desired in applications contemplated herein. However, note that an EO or DEP force not parallel to the flow path can be created by limiting the extension of the electrodes across the bottom wall. This can be done by having both opposite electrodes aligned and separated by a gap of for example 10 micrometers. In this case, a local EO flow can be created for mixing purposes or a local DEP force can be created for trapping particles at a particular location of the flow path.

Figure 10:
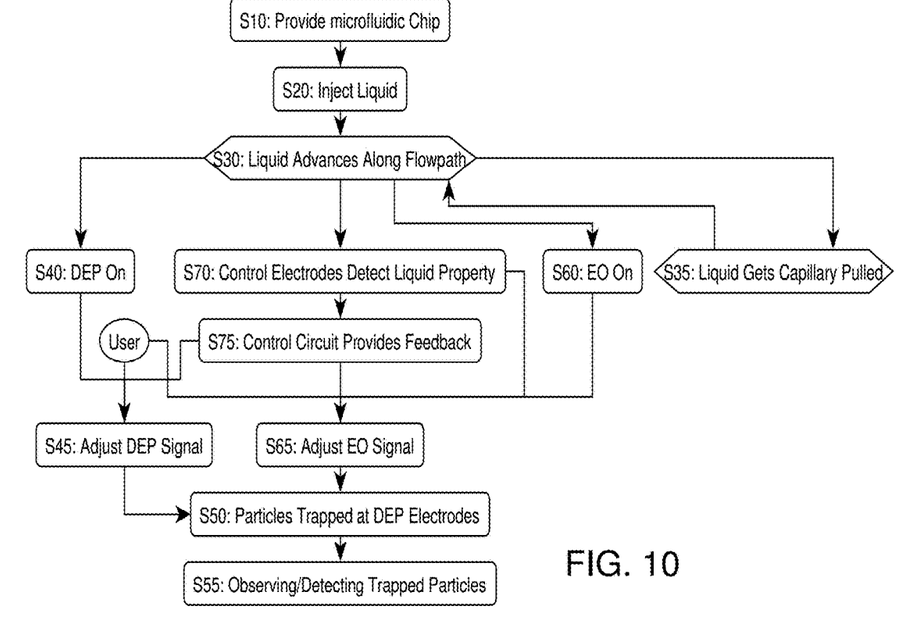
FIG. 10 is a flowchart illustrating high-level steps of a method of operating a chip, according to embodiments.

Next, according to another aspect, the invention can be embodied as methods of operation of a microfluidic chip according to embodiments as described above. One such method is illustrated in the flowchart of FIG. 10. Most generally, such methods revolve around three essential steps, which typically are concomitant (at least partly):

At step S20, a liquid is injected, which liquid comprises a suspension of particles, such as functionalized microbeads;

Step S30: the liquid wets and advances along the flow path 22. It is preferably capillary pulled (step S35) by a passive capillary pump 34 (in fluid communication with the flow path); and Step S40: the DEP circuit is energized, in order to trap particles at the DEP electrodes.

The above method shall typically be completed by observing and or detecting particles trapped at the DEP electrodes (step S55), e.g., by acquisition of a fluorescence signal.

Step S40 is preferably carried out thanks to a DEP signal generator coupled in the DEP circuit to provide a DEP AC signal to the DEP electrodes, by modulating S45 an amplitude and/or a frequency of the DEP AC signal to modulate the DEP force as necessary to trap S50 particles (and e.g., to distribute particles among DEP electrodes).

As illustrated in FIG. 10, DEP trapping is preferably accomplished concurrently with EOF tuning, i.e., while modulating S65 an amplitude and/or a frequency of a EO AC signal provided to EO electrodes of one or more EO circuits. EO AC signal modulation is carried out via one or more EO signal generators, suitably coupled in their respective EO circuits, as described earlier. Still, in some specific implementations, only one AC signal generator may be coupled into several EO circuits (to generate codirectional EO forces). It is accordingly possible to modulate the EO force and obtain an EO force sufficient to alter a flow of liquid advancing in the flow path, and in turn optimize the particle trapping process.

As further seen in FIG. 10, one or more control circuits (having respective control electrodes) may be involved to provide feedback to the EO circuits (steps S70-75). More generally, and as touched earlier, control circuits may similarly couple to the DEP circuit (not shown in FIG. 10). The user may otherwise interact with EO/DEP signal generators to modulate AC signals provided to the EO/DEP electrodes. Different scenarios can be contemplated, ranging from a full user-controlled signal to a full automated signal control.

An example of flow control (event sequence) follows:
1. Sample is loaded (step S10) and starts to flow (S30) in a wettable microchannel toward the capillary pump;
2. Forward EOF (~1 kHz frequency, few V peak to peak amplitude) is switched on (S60) to assist capillary filling (S35). Filling accelerates as more electrode get wetted by liquid (S35+S30);
3. EOF paused (S65, no EOF applied anymore). CDF is driven by filling of capillary pump (S35);
4. Strong backward EOF applied (S65), DEP is switched on (S40). Reversal of flow results (S30), which increases bead localization and exposes them to more analyte from solution;

5. EOF is paused (S65, no EOF, DEP is still on). New plug of sample passing on beads toward capillary pump (S30+S35);
6. Low backward EOF (S65). Liquid slowly filling toward pump (S30+S35) for example for rinsing sample with buffer; and
7. Acquisition of fluorescence signal (S55).

In the above sequence, DEP is switched on (S40) concomitantly with steps 4-5 to ensure trapping of beads (S50). DEP modulation (S45) is performed, notably to briefly release the beads to let them explore the sample volume efficiently on a short distance before trapping them back.

In another example of application, a microfluidic chip system (comprising both DEP and EO circuits) may further comprise an image capture element (e.g., an image sensor array) at a set location along a microchannel. The image capture element can be located parallel to the microchannel and aligned to capture images of a liquid flowing through it. This image capture element is further connected to an electronic circuit, the latter comprising an image processing device and a feedback loop. The image processing device, i.e., comprising both hardware and software components, is configured to identify stages of the fluid flow or particle location. The microfluidic chip system otherwise comprise voltage determination elements, coupled to determine voltage settings of the electrodes, at various locations along the microfluidic channel or channels. The feedback loop serves to control the voltage of the electrodes according to output from image processing and voltage determination elements.

The above embodiments have been succinctly described in reference to the accompanying drawings and may accommodate a number of variants. Several combinations of the above features may be contemplated. Examples are given in the next section.

3. Specific Embodiments/Technical Implementation Details

3.1 Example of Fabrication Methods

3.1.1 Using Thick Resist/Dry-Film for Microfluidic Structures

The substrate can be silicon or glass. Electrodes are patterned on the substrate, e.g., Al (50 nm). Channel patterning is carried out via exposed and developed SU-8 (or dry-film photoresist). The cover can be PDMS, laminate, plastic, etc. The SU-8 is initially hydrophobic, therefore a surface treatment is required, e.g., a 2-3 s cold plasma activation of SU-8 and Si/SiO$_x$ chip for achieving hydrophilic surfaces. Such a fabrication provides relatively low resolution and requires quite demanding photolithography steps to eliminate cracks and delamination. A dry-film resist is easier to process and can be initially hydrophilic, i.e. no need for plasma activation. A similar type of dry-film resist can be used to cover the microfluidic structures. Vias (loading pad and air vents) can be on the cover or silicon.

An example of specifications reflecting the embodiment of FIG. 1 follows, in Table II.

TABLE II

Specifications for device of FIG. 1 (example)

| | |
|---|---|
| Chip size | 1 - few cm$^2$ |
| Chip material | Base: Si/SiO$_x$, Electrodes: Al, Microfluidics structures: 18 μm thick SU-8, Cover: PDMS layer |

TABLE II-continued

Specifications for device of FIG. 1 (example)

| | |
|---|---|
| Sample volume | A few μL up to 20 (or more) μL |
| Assays | Ligand-receptor assays (e.g. fluorescence immunoassays) |
| Flow | Initially CDF then modulated with EOF |
| Signal Localization | DEP trapping of 0.2-10 μm polystyrene beads |
| Surface treatment | 2-3 s cold plasma activation of SU-8 and Si/SiO$_x$ chip |
| Electrical input | EOF: 10 V AC, 1 kHz<br>DEP: 10 V AC, 1 MHz |
| Buffers tested | TRIS 1×, PBS, 1M KCl |
| Comments | Possible to have mixed populations of beads (e.g. 2 and 10 μm) |
| Signal reading | Fluorescence measured through cover using a microscope |

3.1.2 Using Silicon and Electrodes Patterned on Cover

Alternatively, the substrate can be silicon, the cover can be glass and electrodes can be patterned on the cover. Channels are in that case obtained by etching and passivating silicon. More in detail, such an approach requires dry-etching for channels and the vias (long etching process). Electrodes cannot be patterned inside the channels in that case due to vertical sidewall profile. Instead, electrodes are bonded to the cover by way of fusion bonding, which process is rather difficult to optimize.

3.1.2 Fabrication of Recessed Electrodes, Flush with Surrounding Surfaces

As present inventors have realized, the use of thick resists for fabricating microfluidic channels, e.g., for obtaining lateral walls of microchannels, is inconvenient, notably due to their limited temperature and chemical stability. It is furthermore difficult to tailor the surface chemistry of these resists (e.g. for controlling wetting, or the adhesion of biomolecules and cells). In addition, processing thick resists requires using more resist, longer backing, exposure and development steps, and also sometimes requires multiple spin coating steps. The mechanical properties and internal stress of such resists can also be an issue during microfluidic chip fabrication and utilization.

Besides, it is another challenge to pattern metals in and/or across structures having depths around or in excess of 5 micrometers due to (1) the inhomogeneity in thickness of resists (used as sacrificial layers for lift-off) that are deposited across deep structures and (2) the difficulty of patterning metals using lift-off techniques, especially in channels having vertical sidewalls. Inventors concluded to the need for improved methods of fabrication of microfluidic chips, allowing for satisfactorily patterning electrodes (or more generally electrically conductive patterns) thereon, even in and/or across structures having depths around or in excess of 5 micrometers.

General aspects of fabrication methods they devised follow.

In their most general definitions, such methods consider, as a starting point, a structured substrate (e.g., a Si wafer) having a face F covered by an electrically insulating layer (e.g., SiO$_2$). How to obtain such a substrate is the subject of preliminary steps S1-S7, which are discussed below. Several methods for obtaining a structured substrate covered by an electrically insulating layer are otherwise known in the art.

First, a resist layer is obtained, which layer covers one or more selected portions P1 of the electrically insulating layer. Accordingly, there will be at least a remaining portion P2 of the electrically insulating layer that is not covered by the resist layer. The selected portion(s) P1 may be given various possible shapes, resulting in complementary shapes for portion(s) P2, as desired for the electrically conductive layer to be deposited next.

The next step is key: it comprises partially etching a surface of the remaining portion(s) P2 of the electrically insulating layer with a wet etchant E, in order to create a recess and/or an undercut under the resist layer, i.e., at an interface (or border) between the resist and layer.

Then, an electrically conductive layer is deposited on the etched surface. The deposition of the layer is such that the electrically conductive layer reaches the created recess and/or undercut (i.e., without substantially filling the recess/undercut).

Finally, the resist layer can be removed (lift-off), in order to expose a portion P1 of the electrically insulating layer adjoining a contiguous portion P2 of the electrically conductive layer.

By construction, the recess and/or undercut is located at the level of an interface, i.e., a frontier between the electrically insulating layer and the resist layer. This recess and/or undercut furthermore extend along a periphery, or a border of the remaining portion P2. Present inventors realized that such a recess and/or undercut is key for obtaining neat frontiers between the insulating and conductor layers.

In fact, an explanation is that recesses/undercuts substantially lower the risk of defects at the frontier between the conductive and insulator layers, which then enable an easier lift-off (continuous metal film deposition over the resist is prevented), and in turn allows for nicely flush surfaces to be obtained. Importantly, there is no need for a double-layer resist as usually done in the art.

An example of a detailed fabrication method is the following:
1. A silicon wafer is provided, that exhibits <100> crystallographic orientation;
2. Thermal oxidation is performed ($SiO_2$ growth): a $SiO_2$ layer is obtained;
3. Photolithography steps are carried out, to obtain a resist layer covering selected regions R1 of the oxide layer, such that remaining regions R2 of the oxide layer are not covered by the resist layer. As usual, photolithography may involve HDMS priming, photoresist spin-coating, soft-bake, exposure, development, etc. The exposure dose, the development time, and electrode patterns may need to be optimized and pattern correction on mask level is desired to minimize subsequent problems, as known per se in photolithography;
4. The $SiO_2$ mask etching can be done by dry (plasma) or wet etching. Wet etching (BHF) is preferred;
    Wafer preparation may includes a step of photoresist removal (wet or dry), and a short BHF dip to remove the native oxide (beyond oxide already etched in 4.), followed by rinsing with deionized water;
5. Then, anisotropic silicon etching is carried out using TMAH, KOH or EDP. TMAH is preferred since it has higher selectivity over the $SiO_2$ mask, also it does not contaminate the wafer;
6. $SiO_2$ mask removal can be done by dry (plasma) or wet etching. Wet etching (BHF) is again preferred;
7. Thermal oxidation is performed again (the wafer is cleaned from metal and organic contaminants prior to oxidation), now to obtain a uniform, hydrophilic layer, covering notably the microstructures;
8. Photolithography steps are performed again, now for obtaining a resist layer covering selected portions P1 of the $SiO_2$ layer. A closed chamber coating system is preferred for more conformal photoresist coverage;
9. Partial $SiO_2$ etching is done in BHF to partially etch the surface of the remaining portion P2 of layer and create recesses/undercuts under the resist. This creates an undercut and a recess on the $SiO_2$ layer. The etch depth approximately corresponds to the thickness of metal deposited in next step;
10. Metal deposition follows; and
11. The photoresist is etched (lift-off) in an organic solvent, where the metal on the photoresist is lifted-off, leaving metal only inside the patterned regions P2.

3.2 Covering the Chip

After step 11. above, the wafer can be placed on a supporting tape for dicing, the front-side can be protected by a photoresist layer or a tape. At this point, microstructures can still be rinsed, cleaned and dried.

The microfluidic chip can subsequently be covered. In preferred variants, a cover-film is applied to cover the microfluidic structures and possibly complete them (e.g., close channels 20), before dicing.

The cover-film may be applied to cover several chips fabricated in parallel on a same wafer, which is advantageous for large scale fabrication. The cover film 82 is thus applied at substrate-level, after cleaning, and before singulation in that case. The cover film 82 must therefore be distinguished from a protective (photoresist) film that can otherwise be applied before dicing. Indeed, protective films are usually applied before dicing to protect a processed wafer. Since here the cover film 82 is applied after cleaning (e.g., after having rinsed, cleaned and dried the partially cut substrate), clean microfluidic structures are obtained for the whole assembly, i.e., at substrate level, a thing that usually is only carried out at chip level. Once the exposed surface is sealed with the cover film 82, the assembly can be singulated and the resulting dies can be readily used.

Several materials can be contemplated for the cover-film: Of particular interest are dry-film resists (usually optically clear), such as polyepoxide films, which have been found to be best suited for several applications. They notably are rigid enough to tent over the channels 20 without collapsing. They can be easily diced and have good adhesion to the surface to prevent delamination and leaking. Most practical is to use a cover film initially provided as a laminate sheet to apply it on the surface of the substrate. In variants, any rigid enough cover film can be contemplated, like silicon or thin glass (its Young's modulus is typically between 4 and 200 gigapascal). If an optical clear material is required, glass can be used.

According to many test performed by the inventors, best results are obtained if the thickness of the dry-film resist 62 applied is between 10 and 100 μm. Satisfactory results were obtained with 14 μm thick films but optimal results were obtained for thicknesses of about 50 μm (±20 μm), the film itself shall preferably exhibit less than 5% thickness variation.

Sealing is critical for applications that require preventing evaporation and crosstalk of liquids/samples/reagents across different microfluidic structures. Elastosmers such as PDMS were found to contaminate the microfluidic structures, making them hydrophobic due to the surface diffusion of low molecular weight siloxanes. While chips covered with PDMS were useful for experiments and developing the technology, these chips may not have a sufficiently long shelf lifetime stability for optimal logistics that is needed in diagnostics. When optical transparency, chemical stability, low auto-fluorescence in specific optical regions used for fluorescence assays, conformability with surfaces, mechanical strength, water and air non-permeability become critical requirements, then dry-film resists are better suited, being particularly adapted to the sealing of microfluidic structures as fabricated here.

3.3 Specific Embodiment and Application

Additional technical details follow which concern concrete examples of fabrication and application.

The chip measures 23×9.3 mm$^2$ and comprises a loading pad, a microchannel with embedded electrodes, a capillary pump, air vents, a cover film and electrical contacts mating with a card-edge socket. Silicon substrate is used to leverage the micromachining processes as well as the favorable properties of Si and SiO$_2$, such as channel etching with tapered sidewall profile, hydrophilicity of SiO$_2$ for capillary filling, thermal and chemical stability, mechanical robustness, compatibility of SiO$_2$ surface with many biomolecules, and well defined and reliable chemical composition.

In the fabrication process, channels are anisotropically etched in silicon using TMAH and electrically passivated by thermal oxidation. The electrodes were patterned by metal evaporation and lift-off after conformal coating and patterning of a single-layer photoresist. Prior to metal deposition, a short isotropic SiO$_2$ etching is introduced to assist lift-off and to recess the electrodes. The photolithography parameters are optimized to achieve at least a 5-μm minimum feature size in 20 μm deep trenches. Following the dicing and cleaning steps, a hydrophilic dry-film cover is laminated at 45° C. to seal the microfluidic structures. SEM inspection showed that the cover film perfectly tents over the channels and over the capillary pump. The electrodes showed minimized edge defects and very flat surface topography owing to the SiO$_2$ recessing step.

Functionality of the above chip was demonstrated by trapping beads in a liquid filling the chip by capillarity. 10 μm diameter polystyrene beads were suspended in a 1× Tris-EDTA buffer and pipetted to the loading pad while 10 Vpp potential at 1 MHz was applied to the electrode set. The buffer solution filled the channels and pulled the beads towards the DEP trapping region. Beads were trapped on the first electrodes and distributed to the other electrodes by tuning the potential. The experiments showed autonomous flow generation and reproducible bead trapping. The combination of conformal electrode patterning and capillarity-compatible channel fabrication may extend the application areas of advanced and autonomous microfluidic chips for a range of electrokinetics phenomena without adding excessive complexity in design and fabrication.

3.4 Final Remarks

Methods described herein can be used in the fabrication of microfluidic devices, notably wafer-based chips. The resulting chips can for instance be distributed by the fabricator in raw wafer form (that is, as a single wafer that has multiple unpackaged chips), as a bare die, or in a packaged form. In the latter case the chip is mounted in a single chip package (such as a plastic carrier) or in a multichip package. In any case the chip can then be integrated with other chips, or other microfluidic elements (tubing ports, pumps, etc.) even if applications to autonomous chips are preferred, as part of either (a) an intermediate product or (b) an end product.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, other materials could be used for the resist 40 and for the cover-film 82. Also, many variants can be contemplated for the applied AC signals. For instance, pulsed DEP may be used: the DEP force may be pulsed by modulating the DEP AC signal at a much lower frequency (e.g., <10 Hz) than the ~10 MHz DEP signal, e.g., switching it on/off (with a 50% duty-cycle square wave). This provide time-varying DEP forces, a thing that is useful to compete with drag forces, under which particles can be pushed forward or oscillated between two positions.

REFERENCE LIST

1, 1a Microfluidic chip
20 Microfluidic microchannel
20r Reduced transverse section of microchannel
22 Flow path (bottom hydrophilic surface)
22a, 22b, 22c Microchannel inner walls
22a, 22b Microchannel lateral walls
22c Microchannel central (bottom) wall
24 Liquid loading pad
24, 24a, 24b Liquid input (liquid loading pad)
30 Hydrophilic surface portion surrounding electrodes
34 Passive capillary pump
35 Air vent
50 Transverse electrode (e.g., 62,64,66,68) extending across microchannel 20
62, 62a DEP circuit(s)
62a DEP circuit
64b Backward EO
64b, 64f EO circuit
64f Forward EO circuit
66 Physical control electrode
66, 76 Physical control circuit
66, 76; 68, 78 Control circuits
68 Electrochemical control electrodes
68, 78 Electrochemical control circuit
72 DEP signal generator
72c DEP modulation
74 EO signal generator
74c EO modulation
82 Sealing cover

82o Sealing cover opening
E21, E22 DEP electrodes
E41, E42 EO electrodes

The invention claimed is:
1. A microfluidic chip (1, 1a) comprising:
  a flow path (22) defined by a hydrophilic surface;
  a liquid input (24, 24a, 24b) on one side of the flow path;
  at least one electrical circuit (62), hereafter DEP circuit, comprising at least one pair of dielectrophoretic electrodes (E21, E22), hereafter DEP electrodes;
  wherein:
    each of the DEP electrodes extends transverse to the flow path; and
    the DEP circuit is configured to generate a dielectrophoretic force, hereafter DEP force, at the level of the DEP electrodes, and said chip further comprising:
    a further electrical circuit (64b, 64f), hereafter EO circuit, comprising at least one pair of electroosmotic electrodes (E41, E42), hereafter EO electrodes, that extend, each, transverse to the flow path, wherein:
    said at least one pair of DEP electrodes (E21, E22) and said at least one pair of EO electrodes (E41, E42) are at distinct locations in the flow path; and
    the EO circuit is configured to generate an electroosmotic force, hereafter EO force, the EO circuit comprising an EO signal generator (74) coupled in the EO circuit to provide an AC signal to the EO electrodes and configured to enable modulation (74c) of an amplitude and/or a frequency of the AC signal, such that the EO force can be modulated.

2. The microfluidic chip of claim 1, wherein the DEP circuit further comprises a DEP signal generator (72) coupled in the DEP circuit to provide an AC signal to the DEP electrodes and configured to enable modulation (72c) of an amplitude and/or a frequency of the AC signal, such that the DEP force can be modulated.

3. The microfluidic chip of claim 1, wherein the chip (1, 1a) comprises a microfluidic microchannel (20), at least one inner wall (22a, 22b, 22c) of the microchannel defining said hydrophilic surface.

4. The microfluidic chip of claim 3, wherein the microchannel (20) is in fluid communication with a passive capillary pump (34), structured to capillary-drive a flow of water in the hydrophilic flow path, the liquid input being in fluid communication with a liquid loading pad (24), opposite to the capillary pump with respect to the microchannel, and wherein, the chip further comprises a cover (82) sealing at least the microfluidic microchannel and the capillary pump.

5. The microfluidic chip of claim 3, wherein a transverse section (20r) of the microchannel substantially differs at the level of one or more pairs of DEP electrodes of a DEP circuit (62a) of the chip compared to an average transverse section of the microchannel (20), and this transverse section is between 1.5 and 4 times larger or smaller than the average section of the microchannel.

6. The microfluidic chip of claim 5, wherein the transverse section (20r) of the microchannel at the level of one or more pairs of DEP electrodes is between 2 and 3 times larger or smaller than the average section of the microchannel.

7. The microfluidic chip of claim 1, wherein a surface of at least one, and of each, electrode (50) extending transverse to the flow path and exposed to fluid in the flow path, is level with a surrounding surface in the flow path, the misalignment between the exposed electrode surface and the surrounding surface being less than 20 nm.

8. The microfluidic chip of claim 7, wherein the misalignment between the exposed electrode surface and the surrounding surface is less than 10 nm.

9. The microfluidic chip of claim 1, wherein electrodes (E41, E42) of one or more electrical circuits of the chip form a repeating pattern of pairs of contiguous electrodes, the electrodes of said pairs of contiguous electrodes being different, having different dimensions.

10. The microfluidic chip of claim 9, wherein electrodes (E41, E42) of one or more electrical circuits of the chip comprise aluminum.

11. The microfluidic chip of claim 1, further comprising at least one additional electrical circuit (66, 76; 68, 78), hereafter control circuit, having at least one pair of control electrodes (66, 68) extending in the flow path, and further configured to detect a change in an electrochemical or a physical property of a liquid flowing at the level of said pair of control electrodes, said control circuits coupled to provide inputs to the EO circuit, and to the DEP circuit.

12. The microfluidic chip of claim 1, wherein at least one pair of DEP electrodes of a DEP circuit (62, 62a) of the chip is closer to the liquid input (24) than at least one pair of EO electrodes of a EO circuit (64b, 64f) of the chip, and wherein, every pair of DEP electrodes is closer to the liquid input than any pair of EO electrodes.

13. The microfluidic chip of claim 1, wherein said EO circuit is a first EO circuit (64f) comprising at least a first pair of EO electrodes, and the chip further comprises an additional EO circuit (64b) comprising at least a second pair of EO electrodes that extend, each, transverse to the flow path, said first pair of EO electrodes and said second pair of EO electrodes being configured to generate opposite EO forces, and wherein, at least one pair of DEP electrodes is between said first pair of EO electrodes of said first EO circuit and said second pair of said second EO circuit.

14. The microfluidic chip of claim 1, wherein the chip comprises a passive capillary pump (34) in fluid communication with the flow path, and an EO circuit of the chip comprises one or more pair of EO electrodes extending, each, in the capillary pump.

15. The microfluidic chip of claim 1, wherein the chip (1) comprises a microfluidic microchannel (20), defining said hydrophilic flow path, and being in fluid communication with a liquid loading pad (24) at one end and with a capillary pump (34) at another end, wherein the chip further comprises a dry-film cover (82) sealing the microfluidic microchannel and the capillary pump, an air vent (35) being provided in fluid communication with the capillary pump.

16. The microfluidic chip of claim 1, wherein the chip (1a) comprises a microfluidic microchannel (20), defining said hydrophilic flow path, said microchannel further exhibiting lateral slanted walls (22a, 22b), at least one, each, of the electrodes of the DEP circuit and/or an EO circuit of the chip being a multiwall electrode, extending at least partly across the hydrophilic surface and one or each of said slanted walls, level with a surrounding surface (30).

17. A method of operating a microfluidic chip according to claim 1, wherein the method comprises:
  injecting (S20) at the liquid input a liquid comprising a suspension of particles;
  letting (S30) the liquid wet and advance along the hydrophilic flow path and, get capillary pulled (S35) by a passive capillary pump of the chip, in fluid communication with the flow path;
  energizing (S40) the DEP circuit for trapping particles at DEP electrodes, via a DEP signal generator coupled in the DEP circuit to provide a first AC signal to the DEP electrodes, by modulating (S45) an amplitude and/or a frequency of the first AC signal to modulate the DEP force as necessary to trap (S50) particles, and concurrently modulating (S65) an amplitude and/or a frequency of a second AC signal provided to EO electrodes of an EO circuit of the chip, said EO circuit configured to generate an electroosmotic force, said at least one pair of DEP electrodes and said at least one pair of EO electrodes are at distinct locations in the flow path, said second AC signal provided by an EO signal generator coupled in the EO circuit, to modulate an amplitude and/or a frequency of the AC signal to modulate the EO force and obtain an EO force sufficient to alter a flow of liquid advancing in the hydrophilic flow path.

18. The method of claim 17, wherein said particles comprise functionalized microbeads.

19. The microfluidic chip of claim 1, wherein said hydrophilic surface is comprises $SiO_2$.

* * * * *